(12) United States Patent
Myers et al.

(10) Patent No.: US 11,737,912 B2
(45) Date of Patent: *Aug. 29, 2023

(54) SYSTEM AND METHOD FOR COOLING THE BRAIN OF A HUMAN SUBJECT

(71) Applicant: Vivonics, Inc., Bedford, MA (US)

(72) Inventors: Ryan Myers, North Andover, MA (US); Ryan Binette, Billerica, MA (US)

(73) Assignee: Vivonics, Inc., Bedford, MA (US)

( * ) Notice: Subject to any disclaimer, the term of this patent is extended or adjusted under 35 U.S.C. 154(b) by 847 days.

This patent is subject to a terminal disclaimer.

(21) Appl. No.: 16/560,030

(22) Filed: Sep. 4, 2019

(65) Prior Publication Data
US 2020/0015999 A1 Jan. 16, 2020

Related U.S. Application Data

(63) Continuation of application No. 16/242,527, filed on Jan. 8, 2019, now Pat. No. 10,406,022.
(Continued)

(51) Int. Cl.
*A61M 16/10* (2006.01)
*A61M 16/06* (2006.01)
(Continued)

(52) U.S. Cl.
CPC .............. *A61F 7/0085* (2013.01); *A61B 5/01* (2013.01); *A61B 5/6817* (2013.01); *A61F 7/007* (2013.01);
(Continued)

(58) Field of Classification Search
CPC ...... A61F 2007/0002; A61F 2007/0006; A61F 2007/0017; A61F 2007/0056;
(Continued)

(56) References Cited

U.S. PATENT DOCUMENTS 4,007,737 A 2/1977 Paluch
4,232,667 A 11/1980 Chalon et al.
(Continued)

FOREIGN PATENT DOCUMENTS

CN 111685927 B 6/2020
EP 1767273 A1 3/2007
(Continued)

OTHER PUBLICATIONS

Supplementary European Search Report dated Sep. 13, 2021 for European Patent Application No. EP19735705, seven (7) pages.
(Continued)

*Primary Examiner* — Annette Dixon
(74) *Attorney, Agent, or Firm* — Iandiorio Teska & Coleman, LLP

(57) ABSTRACT

A system for cooling the brain of a human subject, includes a cooling subsystem which inputs a flow of air or breathable gas, cool the air or breathable gas, and outputs cooled air or breathable gas which is delivered to a human subject. A flow control device controls a flow rate of the flow of the air or breathable gas input to the cooling subsystem and a flow rate of the cooled air or breathable gas delivered to the human subject. One or more flow rate sensors measure at least a flow rate of flow of cooled air or breathable gas. One or more temperature sensors measure at least a temperature of a brain and the temperature of the flow of cooled air or breathable gas. A controller adjusts a cooling rate, the temperature, and the flow rate of flow of cooled air or breathable gas delivered to the human subject to cool the brain of the human subject.

27 Claims, 6 Drawing Sheets

Related U.S. Application Data

(60) Provisional application No. 62/614,635, filed on Jan. 8, 2018.

(51) Int. Cl.
  *A61F 7/00* (2006.01)
  *A61B 5/01* (2006.01)
  *A61B 5/00* (2006.01)
  *A61M 16/00* (2006.01)
  *A61M 5/44* (2006.01)

(52) U.S. Cl.
  CPC .......... *A61M 5/44* (2013.01); *A61M 16/0003* (2014.02); *A61M 16/024* (2017.08); *A61M 16/0666* (2013.01); *A61M 16/1075* (2013.01); *A61F 2007/0002* (2013.01); *A61F 2007/006* (2013.01); *A61F 2007/0064* (2013.01); *A61F 2007/0095* (2013.01); *A61M 2016/0033* (2013.01); *A61M 2205/3327* (2013.01); *A61M 2205/3368* (2013.01)

(58) Field of Classification Search
  CPC ...... A61F 2007/0063; A61F 2007/0064; A61F 2007/0071; A61F 2007/0086; A61F 2007/0088; A61F 2007/0091; A61F 2007/0095; A61F 2007/0096; A61F 2007/0228; A61F 2007/0288; A61F 2007/126; A61F 7/007; A61F 7/0085; A61F 7/12; A61F 7/123; A61M 16/04; A61M 16/0459; A61M 16/0461; A61M 16/0475; A61M 16/0479; A61M 16/0493; A61M 16/0495; A61M 16/06; A61M 16/0683; A61M 16/1075; A61M 19/00; A61M 2016/0039; A61M 2202/0208; A61M 2205/3331; A61M 2205/3368; A61M 2205/3606; A61M 2205/362; A61M 2210/0618; A61M 2210/0693
  See application file for complete search history.

(56) References Cited

U.S. PATENT DOCUMENTS

| | | | |
|---|---|---|---|
| 4,381,267 A | 8/1983 | Jackson | |
| 4,398,535 A | 8/1983 | Guibert | |
| 4,552,142 A | 11/1985 | Hoffman et al. | |
| 4,708,831 A | 11/1987 | Isworth et al. | |
| 4,727,871 A | 3/1988 | Smargiassi et al. | |
| 4,987,896 A * | 1/1991 | Nakamatsu | A61B 5/02416 128/897 |
| 5,527,822 A | 6/1996 | Scheiner | |
| 5,596,987 A | 1/1997 | Chance | |
| 5,676,133 A | 10/1997 | Hickle et al. | |
| 5,722,393 A | 3/1998 | Bartel et al. | |
| 5,795,307 A | 8/1998 | Krueger | |
| 5,881,178 A | 3/1999 | Tsykalov et al. | |
| 5,927,273 A | 7/1999 | Federowicz et al. | |
| 5,976,574 A | 11/1999 | Gordon | |
| 5,997,484 A | 12/1999 | Sugahara | |
| 6,131,571 A | 10/2000 | Lampotang et al. | |
| 6,196,222 B1 | 3/2001 | Heinonen et al. | |
| 6,484,719 B1 * | 11/2002 | Berthon-Jones | A61M 16/024 128/204.23 |
| 6,736,837 B2 | 5/2004 | Fox | |
| 6,983,749 B2 | 1/2006 | Kumar et al. | |
| 6,997,184 B2 | 2/2006 | Donohue | |
| 7,187,960 B2 | 3/2007 | Abreu | |
| 7,318,834 B2 | 1/2008 | Njemanze | |
| 7,547,283 B2 | 6/2009 | Mourad et al. | |
| 7,824,436 B2 | 11/2010 | Barbut et al. | |
| 8,015,974 B2 | 9/2011 | Christopher et al. | |
| 8,075,605 B2 | 12/2011 | Barbut et al. | |
| 8,157,767 B2 | 4/2012 | Rozenberg et al. | |
| 8,167,923 B2 | 5/2012 | Barbut et al. | |
| 8,211,031 B2 | 7/2012 | Poupko et al. | |
| 8,267,092 B2 | 9/2012 | White et al. | |
| 8,308,786 B2 | 11/2012 | Rozenberg et al. | |
| 8,631,799 B2 | 1/2014 | Davenport et al. | |
| 8,696,725 B2 | 4/2014 | Kulstad et al. | |
| 8,851,076 B2 | 10/2014 | White et al. | |
| 8,932,339 B2 | 1/2015 | Harikrishna et al. | |
| 9,138,181 B2 | 9/2015 | Daisley et al. | |
| 9,295,795 B2 | 3/2016 | Christopher et al. | |
| 9,320,644 B2 * | 4/2016 | Kreck | A61M 16/0409 |
| 9,393,378 B2 | 7/2016 | Fearnot et al. | |
| 9,622,908 B2 | 4/2017 | Fontaine | |
| 9,629,745 B2 | 4/2017 | Harikrishna et al. | |
| 9,744,071 B2 | 8/2017 | Harikirshna et al. | |
| 9,795,758 B2 | 10/2017 | Ahmad et al. | |
| 9,826,913 B2 | 11/2017 | Galea | |
| 9,987,162 B2 | 6/2018 | Lee et al. | |
| 10,016,573 B2 | 7/2018 | Shushunov | |
| 10,285,630 B2 | 5/2019 | Takagi | |
| 10,406,022 B2 | 9/2019 | Myers et al. | |
| 10,434,275 B2 | 10/2019 | Hadash | |
| 11,109,999 B2 | 9/2021 | DeMore, Jr. et al. | |
| 11,173,063 B2 | 11/2021 | Zhu | |
| 11,173,261 B2 | 11/2021 | Burgess et al. | |
| 11,229,766 B2 | 1/2022 | Sweeney et al. | |
| 11,400,249 B2 | 8/2022 | White et al. | |
| 11,523,937 B2 | 12/2022 | Harikrishna et al. | |
| 2002/0033178 A1 | 3/2002 | Farrell et al. | |
| 2003/0131844 A1 * | 7/2003 | Kumar | A61M 16/0081 128/200.24 |
| 2004/0087863 A1 | 5/2004 | Eide | |
| 2004/0260229 A1 | 12/2004 | Meir | |
| 2005/0065581 A1 * | 3/2005 | Fletcher | F28F 3/12 607/104 |
| 2005/0119602 A1 | 6/2005 | Murphy et al. | |
| 2005/0187488 A1 | 8/2005 | Wolf | |
| 2006/0112698 A1 | 6/2006 | Cazzini et al. | |
| 2006/0135878 A1 | 6/2006 | Wright et al. | |
| 2006/0276552 A1 | 12/2006 | Barbut et al. | |
| 2007/0021808 A1 | 1/2007 | Rojas | |
| 2007/0162097 A9 | 7/2007 | Rojas | |
| 2007/0213619 A1 | 9/2007 | Inder | |
| 2008/0004613 A1 | 1/2008 | Barbut et al. | |
| 2008/0015543 A1 | 1/2008 | Wang | |
| 2008/0077023 A1 | 3/2008 | Campbell et al. | |
| 2008/0202516 A1 | 8/2008 | Harvie | |
| 2008/0249188 A1 | 10/2008 | Barbut et al. | |
| 2008/0287753 A1 | 11/2008 | Parlikar et al. | |
| 2008/0287812 A1 | 11/2008 | Parlikar et al. | |
| 2008/0294507 A1 | 11/2008 | Reiner | |
| 2009/0056716 A1 | 3/2009 | Carrier | |
| 2009/0143656 A1 | 6/2009 | Manwaring et al. | |
| 2009/0174092 A1 | 7/2009 | Kwok et al. | |
| 2009/0234245 A1 | 9/2009 | Jaffe et al. | |
| 2009/0326345 A1 | 12/2009 | Jaffe et al. | |
| 2010/0005572 A1 | 1/2010 | Chaplin | |
| 2010/0063405 A1 | 3/2010 | Kashif et al. | |
| 2010/0108063 A1 | 5/2010 | Koch et al. | |
| 2010/0210958 A1 | 8/2010 | Manwaring et al. | |
| 2010/0268096 A1 | 10/2010 | Berka et al. | |
| 2010/0292765 A1 | 11/2010 | Etwil | |
| 2010/0312315 A1 | 12/2010 | Ewil | |
| 2010/0331684 A1 | 12/2010 | Ragauskas et al. | |
| 2011/0201962 A1 | 8/2011 | Grudic et al. | |
| 2012/0031405 A1 * | 2/2012 | Geist | A61F 7/0085 128/204.15 |
| 2012/0080031 A1 | 4/2012 | Belson | |
| 2013/0000642 A1 | 1/2013 | Fearnot et al. | |
| 2013/0030411 A1 | 1/2013 | Kreck et al. | |
| 2013/0073015 A1 | 3/2013 | Rozenberg | |
| 2013/0150687 A1 | 6/2013 | Kato | |
| 2013/0274615 A1 | 10/2013 | Ben-Ari et al. | |
| 2014/0060534 A1 | 3/2014 | Belson | |
| 2014/0373842 A1 | 12/2014 | Ahmad et al. | |
| 2016/0058395 A1 | 3/2016 | Muser et al. | |
| 2016/0128587 A1 | 5/2016 | Kuenen et al. | |
| 2016/0174858 A1 | 6/2016 | Galea | |

(56) References Cited

U.S. PATENT DOCUMENTS

| | | |
|---|---|---|
| 2016/0192849 A1 | 7/2016 | Galea |
| 2016/0270952 A1* | 9/2016 | Vergara ............... A61F 7/02 |
| 2016/0296365 A1* | 10/2016 | Kreck ................. A61F 7/12 |
| 2017/0143538 A1 | 5/2017 | Lee et al. |
| 2017/0266037 A1 | 9/2017 | Belson |
| 2018/0110449 A1 | 4/2018 | Maeda et al. |
| 2018/0153737 A1 | 6/2018 | Harikrishna et al. |
| 2019/0151142 A1* | 5/2019 | Kreck ............. A61M 16/0409 |
| 2020/0015999 A1 | 1/2020 | Myers et al. |
| 2020/0113461 A1 | 4/2020 | Sanz Garcia et al. |
| 2021/0128347 A1 | 5/2021 | Lipford et al. |
| 2022/0192866 A1 | 6/2022 | Burgess |
| 2023/0084620 A1 | 3/2023 | Andis et al. |

FOREIGN PATENT DOCUMENTS

| | | | |
|---|---|---|---|
| EP | 2547389 B1 | 4/2016 | |
| KR | 20130106207 A | 9/2013 | |
| WO | WO-9623544 A1 * | 8/1996 | ............... A01N 1/02 |
| WO | 2008144490 A1 | 11/2008 | |
| WO | 2009029386 A1 | 3/2009 | |
| WO | 2011103102 A1 | 8/2011 | |
| WO | 2013079227 A1 | 6/2013 | |
| WO | 2016023920 A1 | 2/2016 | |
| WO | 2016059173 A1 | 4/2016 | |
| WO | 2016164891 A1 | 10/2016 | |
| WO | 2022114645 A1 | 2/2022 | |

OTHER PUBLICATIONS

Written Opinion of the International Searching Authority for International Application No. PCT/US2019/012706 dated Mar. 22, 2019 (eight (8) pages).

Springborg et al., "First Clinical Experience with Intranasal Cooling for Hyperthermia in Brain-Injured Patients", Neurocritical Care, 18(3): pp. 400-405, 2013.

Takeda et al., "Effects of Pharyngeal Cooling on Brain Temperature in Primates and Humans. A Study for Proof of Principle", Anesthesiology, V.117(1): pp. 117-125, 2012.

Andrews et al., "European Society of Intensive care Medicine Study of Therapeutic Hypothermia (32-35 C) for Intracranial Pressure reduction After Traumatic Brain Injury (the Eurotherm: 3235Trial)", Trials 12:8, (Thirteen (13) pages total), 2011.

Abou-Chebl et al., "Local Brain Temperature reduction Through Intranasal Cooling With The RhinoChill Device", Stroke 42(8), pp. 2164-2169, 2011.

* cited by examiner

SYSTEM AND METHOD FOR COOLING THE BRAIN OF A HUMAN SUBJECT

RELATED APPLICATIONS

This application is a continuation of U.S. patent application Ser. No. 16/242,527 filed Jan. 8, 2019, which hereby claims the benefit of and priority to U.S. Provisional Application Ser. No. 62/614,635 filed Jan. 8, 2018, under 35 U.S.C. §§ 119, 120, 363, 365, and 37 C.F.R. § 1.55 and § 1.78, and both applications are incorporated herein by this reference.

GOVERNMENT RIGHTS

This invention was made with government support under Contract No. M67854-17-C-6548 awarded by the Department of Defense. The government has certain rights in the invention.

FIELD OF THE INVENTION

This invention relates to a system and method for cooling the brain of a human subject.

BACKGROUND OF THE INVENTION

Initial traumatic brain injury (TBI) may cause immediate damage to cerebral structure, neurons, or vasculature. Secondary injuries that follow TBI may include ischemia, swelling, cerebral edema, and increased intracranial pressure. In general, these secondary complications may lead to reduction in the supply of oxygenated blood to the brain (brain ischemia) which may lead to neurodegeneration. In addition to TBI, brain ischemia may be caused by stroke, cardiac arrest, and respiratory failure, the three leading causes of death in the United States.

The secondary injury mechanism following a traumatic event generally results in cell death from lack of blood and will typically begin after about 30 minutes of disrupted blood supply. Prolonged oxygen deprivation may cause failure of autoregulation and programmed cell death. Thus, it is important that intervention is performed within the first 6 hours after the initial injury.

Evidence suggests that selectively cooling the brain temperature to about 32-35° C. (therapeutic hypothermia), (See e.g., Andrews et al., *European Society of Intensive Care Medicine Study of Therapeutic Hypothermia (32-35 C) for Intracranial Pressure Reduction After Traumatic Brain Injury (The Eurotherm3235Trial)*, Trials 12(1): 8, (2011), incorporated by reference herein) or maintaining brain temperature in the normal range (target temperature management) early in the therapeutic window, e.g., less than about 30 minutes after injury, may delay necrotic cell death and apoptotic cell death. This may lead to positive effects including, inter alia, a lower cerebral metabolism which reduces harmful metabolic byproduct build up resulting from inadequate blood flow, reduced cerebral oxygen requirements, prevention of neurogenic fever, reduced intracranial pressure (ICP) encephalitis, and the like.

There are currently Class 1 and Class 2 recommendations for therapeutic hypothermia (TH) and target temperature management (TTM) after certain ischemic brain injuries. Target temperature management and therapeutic hypothermia has been indicated for several ischemic injuries and evidence. See, e.g., Abou-Chebl et al., *Local Brain Temperature Reduction Through Intranasal Cooling With the RhinoChill Device*, Stroke 42(8): 2164-2169, (2011), Takeda et al., *Effects of Pharyngeal Cooling on Brain Temperature In Primates and Humans A Study for Proof of Principle*, The Journal of the American Society of Anesthesiologists, 117 (1): 117-125.2012, (2012), and Springborg et al., *First Clinical Experience With Intranasal Cooling for Hyperthermia in Brain-injured Patients*, Neurocritical care, 18(3): 400-405, (2013), all incorporated by reference herein. All Class 1 Level of Evidence (LOE) B—Class III LOE C points towards increased favorable outcomes, reduced length of ICU stay, and improved neurological function at about 6 months after injury.

One conventional system for cooling tissue is disclosed in U.S. Publ. No. 2013/0000642 to Fearnot et al., incorporated by reference herein. Disclosed in the '642 patent application is a system which relies on forced air that is not cooled. Even if the '642 patent application is capable of cooling the forced are, the mask apparatus as taught by the '642 patent application may not provide sufficient cooling to cool the brain of a human subject. Additionally, the '642 patent application fails to teach any feedback to provide any type of control over a cooling process.

Another conventional method and device for non-invasive cerebral systemic cooling is disclosed in U.S. Pub. No. 2006/0276552, incorporated by reference herein. The '655 patent application teaches a complicated and cumbersome cooling device and method which relies inserting an elongated member into a nasal cavity of a patient, injecting a perfluorocarbon spray and a gas into the nasal cavity, and using the gas to enhance evaporation of the perfluorocarbon to reduce the temperature of the brain or infusing a cooled liquid through a complicated three-part cooling assembly with a balloon and two elongated tubes placed inside the nose.

Studies on the effectiveness of brain temperature management after traumatic brain injury is extremely limited. Due to the technological limitation of conventional systems and methods, the evidence in support of conventional systems and methods to address TTM and TH exhibit at least the following drawbacks: studies examine whole body cooling rather than selective cooling of the brain which may have adverse side effects such as shivering, cooling may not be initiated within 30 minutes of injury, and consistent cooling and rewarming protocols are not followed.

Thus, there is a need for a less complex and less cumbersome system and method for cooling the brain that provides a flow of air or breathable gas that cools the brain to effectively provide TH and TTM at the point of injury or prior to hospitalization and early in the therapeutic window, monitors the temperature of the brain and human subject, and adjusts temperature and flow rate of the flow of air or breathable gas to reduce possible adverse side effects which may be associated with cooling the brain of a human subject.

SUMMARY OF THE INVENTION

In one aspect, a system for cooling the brain of a human subject is featured. The system includes a cooling subsystem configured to input a flow of air or breathable gas, cool the air or breathable gas, and output cooled air or breathable gas to a line coupled to a device adapted to deliver the cooled air or breathable gas to a human subject. A flow control device coupled to the cooling subsystem is configured to control a flow rate of the flow of the air or breathable gas input to the cooling subsystem and a flow rate of the cooled air or breathable gas output to the line. One or more flow rate sensors coupled to the cooling subsystem is configured to measure at least a flow rate of flow of cooled air or breathable gas. One or more temperature sensors are configured to measure at least a temperature of a brain or a brain correlative site of the human subject and the temperature of the flow of cooled air or breathable gas. A controller is coupled to the cooling subsystem, the flow control device, the one or more flow rate sensors, and the one or more temperature sensors. The controller is configured to adjust a cooling rate, the temperature, and the flow rate of flow of cooled air or breathable gas delivered to the human subject based on at least the measured temperature of the brain or the brain correlative site and the measured flow rate of the flow of cooled air or breathable gas to cool the brain of the human subject.

In one embodiment, the controller may be configured to adjust the temperature and the flow rate of the flow of cooled air or breathable gas to provide therapeutic hypothermic (TH) and/or target temperature management (TTM) to normothermic levels. The controller may be configured to control the flow control device to provide a flow rate of the cooled air or breathable gas at flow rate in the range of about 0 L/min to about 50 L/min. The cooling subsystem cooling subsystem may be configured to input the air or breathable gas having a temperature in the range of about −10° C. to about 10° C. The controller may be configured to control the cooling subsystem to cool the air or breathable gas and provide the flow of cooled air or breathable gas delivered to the human subject having a temperature in the range of about −14° C. to about 7° C. The one or more temperature sensors may include a tympanic sensor or temporal artery sensor. The device adapted to deliver the cooled air or breathable gas to a human subject may include a nasal cannula. The one or more temperature sensors may be adapted to be placed on an end of the nasal cannula. The controller may be configured to control the flow control device to adjust a pressure of the flow of cooled air or breathable gas. The cooling subsystem may include a gas block comprised of a thermally conductive material, the gas block including an inlet configured to input the flow of air or breathable gas and an outlet configured to output the flow of cooled air or breathable gas. The air block may include a plurality of flow channels comprised of the thermally conductive material configured to cool the flow of air or breathable gas and provide and direct the flow of cooled air or breathable gas to the outlet. The cooling subsystem may include a heat transfer subsystem coupled to the gas block and configured as a thermal electric cooling (TEC) device. The controller may be configured to control a current or voltage applied to the TEC to provide a cooling temperature on a side of the TEC in contact with the gas block to cool the source of the flow of air or breathable gas and provide the flow of cooled air or breathable gas or to provide a heating temperature on a side of the TEC in contact with the gas block to heat the source of the flow of air or breathable gas to increase the temperature of the flow of cooled air or breathable gas. The system may include a heat exchange transfer subsystem coupled to the heat transfer subsystem configured to remove heat from the heat transfer subsystem. The heat exchange transfer subsystem may include a conductor block coupled to a side of the TEC and conductive pipes coupled to conductive fins. The system may include a fan coupled to the conductive fins.

In another aspect, a method for cooling the brain of a human subject is featured. The method includes receiving a flow of the air or breathable gas. The air or breathable gas is cooled. A flow of cooled air or breathable gas is output to a line coupled to a device adapted to deliver the cooled air or breathable gas to a human subject. A flow rate of the flow of the air or breathable gas and a flow rate of the cooled air or breathable gas output to the line is controlled. At least a flow rate of flow of cooled air or breathable gas is measured. At least a temperature of a brain or a brain correlative site of the human subject and a temperature of the flow of cooled air or breathable gas is measured. A cooling rate, the temperature, and the flow rate of flow of cooled air or breathable gas delivered to the human subject is adjusted based on at least the measured temperature of the brain or the brain correlative site and the measured flow rate of the flow of cooled air or breathable gas to cool the brain of the human subject.

In one embodiment, the method may include adjusting the temperature and the flow rate of the flow of cooled air or breathable gas to provide therapeutic hypothermic (TH) and target temperature management (TTM) to normothermic levels. The method may include providing a flow rate of cooled air or breathable gas at a flow rate in the range of about 0 to about 50 L/m. The method may include receiving the flow of the air or breathable gas having a temperature in the range of about −10° C. to about 10° C. The method may include cooling the flow of the air or breathable gas to a temperature in the range of about −14° C. to about 7° C. The device adapted to deliver the flow of the air or breathable gas to the human subject may include a nasal cannula. The method may include adjusting a pressure of the flow of cooled air or breathable gas. The method may include providing a gas block comprised of a thermally conductive material, the gas block including an inlet to receive the flow of air or breathable gas and an outlet configured to output the flow of cooled air or breathable gas. The method may include providing a heat transfer subsystem coupled to the gas block configured as a thermal electric cooling (TEC) device. The method may include controlling a current or voltage applied to the TEC to provide a cooling temperature on a side of the TEC in contact with the gas block to cool the source of flow of air or breathable gas and provide a flow of cooled air or breathable gas or to provide a heating temperature on a side of the TEC in contact with the gas block to heat the source of flow of air or breathable gas to increase the temperature of the flow of cooled air or breathable gas. The method may include providing a heat exchange transfer subsystem coupled to the heat transfer system configured to remove heat from the heat transfer subsystem.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
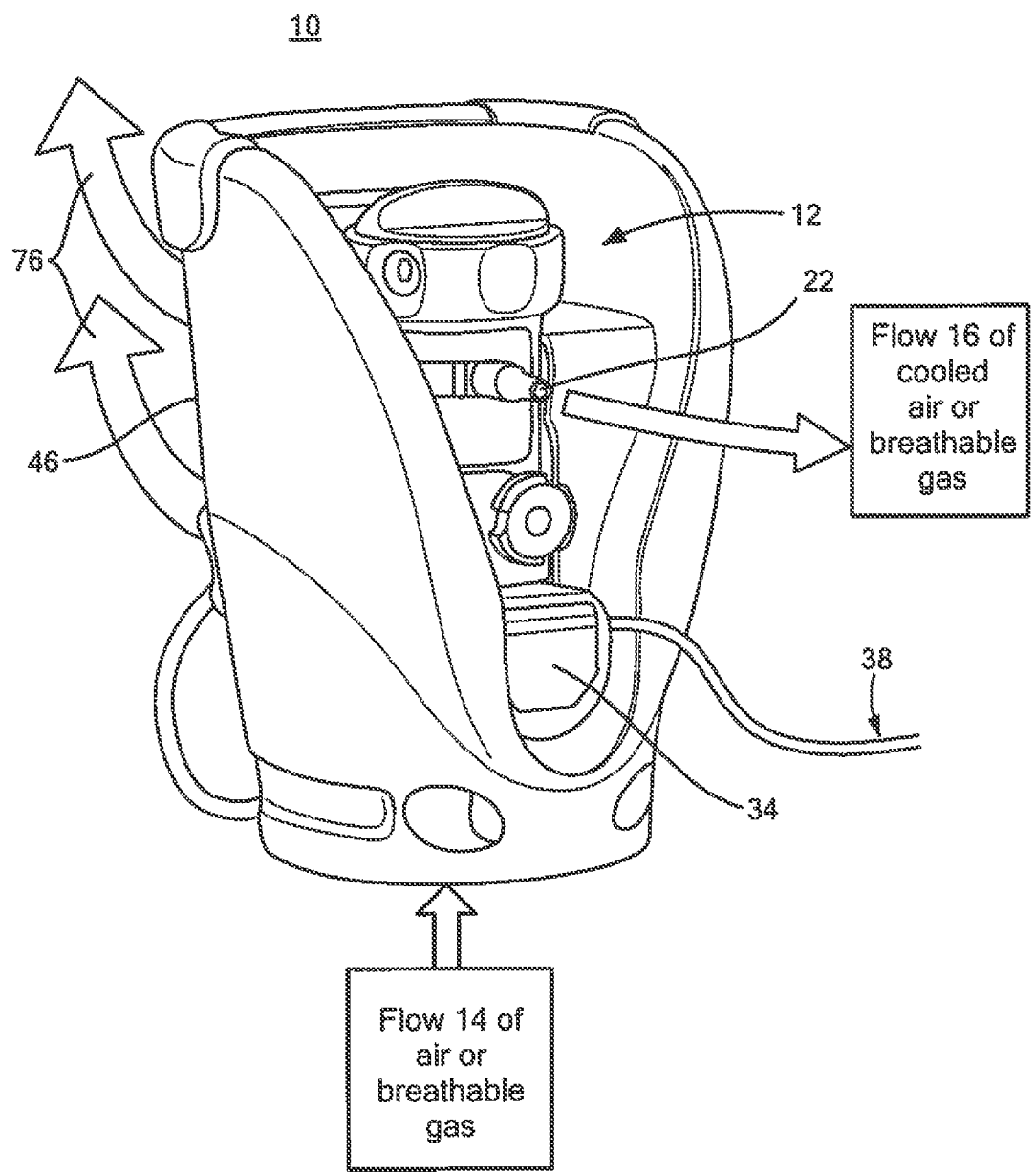
FIG. 1 is a three-dimensional view showing the primary components of one embodiment of the system for cooling the brain of a human subject.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1 one embodiment of system 10 and the method thereof for cooling the brain of a human subject. System 10 includes cooling subsystem 12, shown in greater detail in FIGS. 2, 3, 4, and 5, configured to input or receive flow 14, FIG. 1, of air or breathable gas, cool flow 14 of air or breathable gas, and output flow 16 of cooled air or breathable gas. In this example, cooling subsystem 12 receives flow 14 of air or breathable gas from a source of air or breathable gas (e.g., liquid oxygen) located vessel 17, FIG. 2, coupled to cooling subsystem 12 as shown. In other examples, the source of flow 14 of air or breathable gas may be provided by an air or gas compressor which may reduce cost and improve safety when compared using liquid air or air or breathable gas, such as oxygen. In one example, a 1,200 psi, 4.6 gallon portable air compressor rated 2.2 cubic feet per minute (CFM) at 90 psi may be utilized to provide about supply pressure of flow 14 of air or breathable gas at about 0 to about 50 L/min. In other examples, flow 14 of air or breathable gas may be the air or breathable gas lines at a hospital or similar type facility. In another example, a small blower or small compressor that provides about 0 to about 50 L/min (LPM) at low psi (e.g., less than about 10 psi) may be used within a portable housing, e.g., housing 46, FIG. 2, which preferably houses the primary components of system 10.

Figure 2:
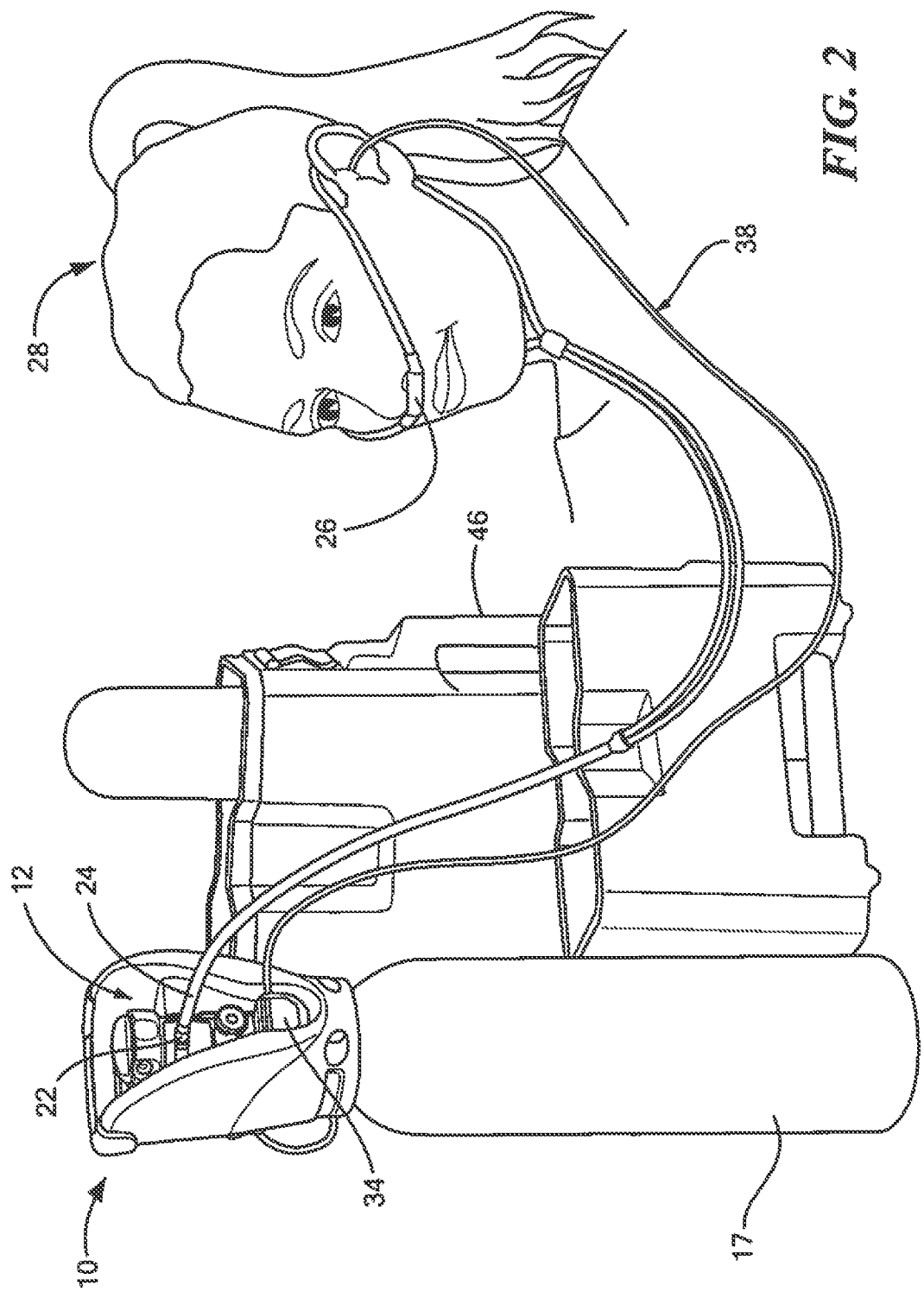
FIG. 2 is a three-dimensional view showing in one example of the source of air or breathable gas input to the cooling subsystem shown in FIG. 1.
Figure 3:
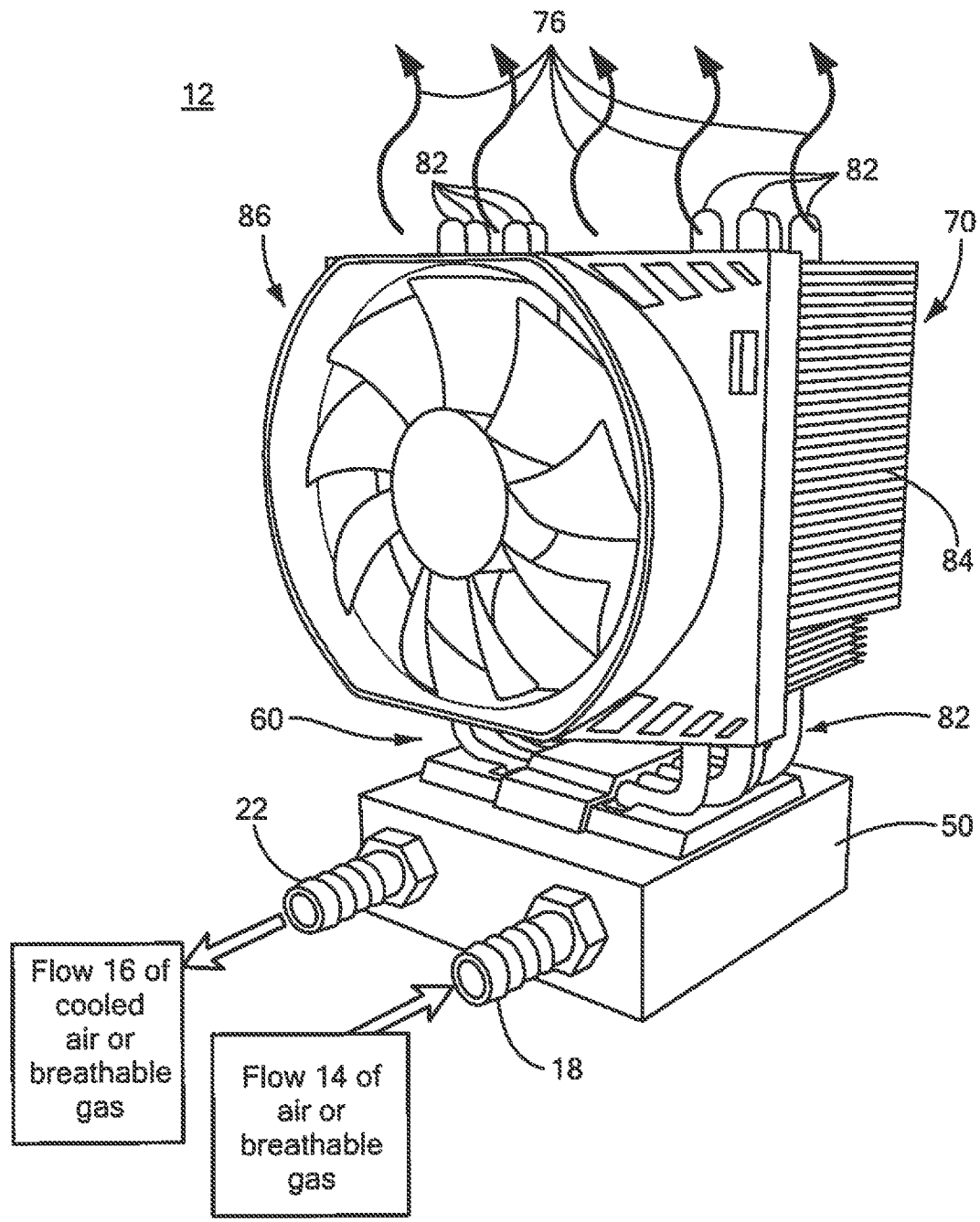
FIG. 3 is a three-dimensional view showing in further detail one example of the cooling subsystem shown in FIGS. 1 and 2.

In one design, cooling subsystem 12, shown in greater detail in FIG. 3, receives flow 14 of air or breathable gas from the source of air or breathable gas discussed above at input 18, cools flow 14 of air or breathable gas, and outputs flow 16 of cooled air or breathable gas at outlet 22, as shown. Outlet 22, also shown in FIGS. 1 and 2, is preferably coupled to line 24, FIG. 2, which preferably delivers flow 16 of cooled air or breathable gas to a device adapted to deliver flow 16 of cooled air or breathable gas to human subject 28, e.g., a nasal cannula, as shown, or similar type device, to provide effective cooling of the brain of the human subject 28 and provide TH and TTM to normothermic levels at the point of injury or prior to hospitalization early in the therapeutic window, e.g., less than about 30 minutes, as discussed in further detail below.

Figure 4:
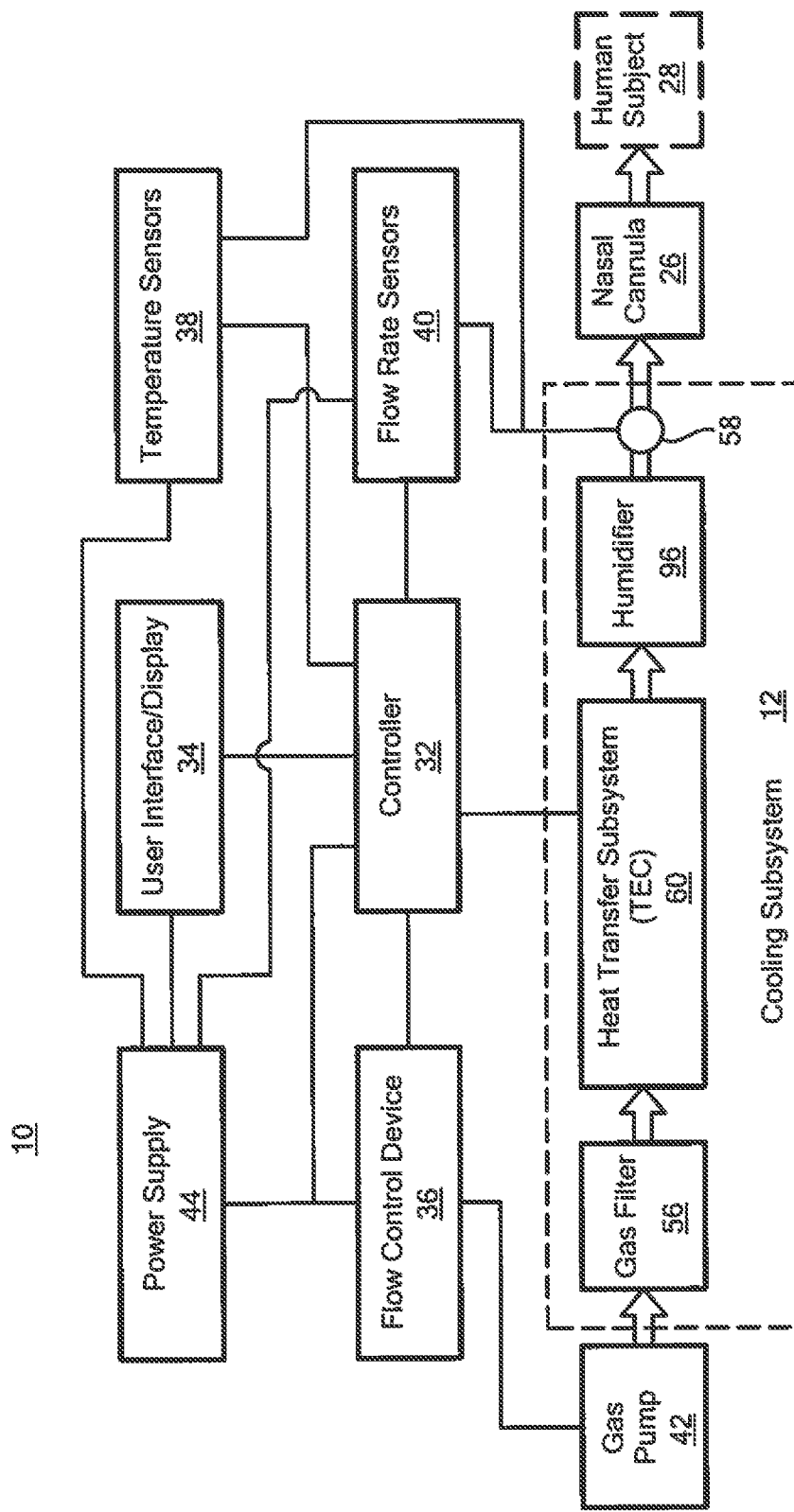
FIG. 4 is a schematic block diagram showing in further detail the primary components of the system for cooling the brain of a human subject shown in one or more of FIGS. 1-3.

System 10 also includes flow control device 36, FIG. 4, coupled to cooling subsystem 12. Flow control device 36 is configured to control a flow rate of the flow 14 of air or breathable gas input to cooling subsystem 12 at input 18, FIG. 2, and a flow rate of flow 16 of cooled air or breathable gas output at 22 and coupled to line 24. In one example flow 14 of air or breathable gas and flow 16 of cooled air or breathable gas are preferably provided by flow control device 36 at a flow rate in the range of about 0 to about 50 L/min.

System 10, shown in one or more of FIGS. 1-4, also includes one or more flow rate sensors 40, FIG. 4, coupled to cooling subsystem 12 which are configured to measure at least a flow rate of flow 14 of air or breathable gas and flow 16 of cooled air or breathable gas.

System 10 also includes one or more temperature sensors 38 configured to measure at least a temperature of the brain of human subject 28, FIG. 2, or the temperature of a brain correlative site of human subject 23, the temperature of flow 14, FIGS. 1 and 3, of air or breathable gas and the temperature of flow 16 of cooled air or breathable gas. The temperature of the flow 16 of cooled air or breathable gas is preferably measured by one or more temperature sensors 38 at point 58, FIG. 4, e.g., at output 22, FIGS. 1-3, such that the temperature of flow 16 of cooled air or breathable gas in line 24, FIG. 2, entering the device adapted to deliver flow 16 of cooled air or breathable gas to human subject 28, e.g., nasal cannula 26 can be controlled, as discussed below. The temperature at the end of nasal cannula 26 is also preferably measured by one or more temperature sensors 38, FIG. 4, placed at the end of nasal cannula 26 and the temperature of the brain or a brain correlative site of human subject 28 is also preferably measured with one or more temperature sensors 38, e.g., a tympanic sensor, FIGS. 1-2, placed in the ear of human subject, FIG. 2, as shown, or a temporal artery sensor, or similarly type temperature sensor, configured to measure the temperature of the brain or a brain correlative site of human subject 28. System 10 also includes controller 32, FIG. 4, coupled to cooling subsystem 12, flow control device 36, one or more flow rate sensors 40, and one or more temperature sensors 38. Controller 32 is configured to adjust a cooling rate, the temperature, and the flow rate of flow 16, FIGS. 1 and 3, of cooled air or breathable gas delivered to human subject 28, FIG. 2, based on at least the measured temperature of the brain and the measured flow rate of the flow 16 of cooled air or breathable gas to cool the brain of the human subject. System 10, FIGS. 1, 2 and 4 also preferably includes user interface/display 34. System 10 also preferably includes air or gas pump 42, FIG. 4, coupled to flow control device 36 and cooling subsystem 12 as discussed above.

In one example, controller 32 is preferably configured to automatically adjust the cooling rate, the temperature, and the flow rate of flow 16 of cooled air or breathable gas FIGS. 1 and 3, based on feedback information provided the one or more temperature sensors 38 configured to measure the temperature of the brain of human subject 28 and one or more flow rate sensors 40 which measure the flow rate of flow 16 of cooled air or breathable gas indicated at 58, FIG. 4. In one example, feedback control for controller 32 may be from one or more temperature sensors 38 configured to measure the temperature of the brain or a brain correlative site, similar to a Proportional, Integral, Derivative (PID), as known by those skilled in the art.

Controller 32 is also preferably configured to control flow control device 36 to adjust the pressure of flow 14 of air or breathable gas and flow 16 of cooled air or breathable gas.

In one example, one or more flow rate sensors 40 may be an air flow gage which provides flow rate information about the flow rate of flow 16 of cooled air or breathable gas at point 58 to controller 32 which controls flow control device 36 coupled to air or gas pump 42 to provide a flow rate of flow 14 of air or breathable gas and flow 16 of cooled air or breathable gas preferably in the range of about 0 to 50 L/min, as discussed above, or similar type flow rate as needed to cool the brain of human subject 28. Air or gas pump 42 may include a blower preferably configured to sweep flow 16 of cooled air or breathable gas, FIG. 3, in line 24, FIG. 2, rapidly using fans or similar type devices, radially, linearly. In other designs, air or gas pump 42 may include various embodiments of a compressor as discussed above which, in one example provides a supply pressure of flow 14 of air or breathable gas at about 0 to 50 L/min. The compressor may include linear, diaphragm, turbine, radial blower or other designs configured to provide an elevated pressure and flow rate of flow 14 of air or breathable gas and flow 16 of cooled air or breathable gas. In other examples, air or gas pump 42 may be a supply line of air or air or breathable gas from a hospital facility or similar type supply line.

System 10 also includes and power supply 44 coupled to controller 32 which preferably provides power to controller 32 and power for cooling subsystem 12, one or more temperature sensors 38, flow control device 36, one or more flow rate sensors 40 and user interface display 34 of system 10. In one example, power supply 44 may be a battery, e.g., a nickel metal hydride battery, a lithium ion battery, a lithium polymer, or similar type battery.

As discussed above, the flow rate of flow 16 of cooled air or breathable gas, FIGS. 1-3 provided by cooling subsystem 12, is preferably in the range of about 0 to about 50 L/min. In other examples, the flow rate of flow 16 of cooled air or breathable gas, provided by cooling subsystem 12 may be greater or less than 50 L/min. In one example, about 0.8 cubic feet per minute (CFM) of flow 16 of cooled air or breathable gas may be provided by cooling subsystem 12 and delivered to human subject 28 to effectively cool the brain of human subject 28. In one example, cooling subsystem 12 is configured to cool flow 14 of air or breathable gas at a temperature in the range of about −14° C. to about 7° C. to provide flow 16 of cooled air or breathable gas at a temperature of about −10° C. to about 10° C. to effectively and efficiently cool the brain of human subject 28.

The intranasal cooling using forced flow 16 of cooled air or breathable gas provided by system 10 discussed above provides an effective approach for achieving clinically significant brain cooling to provide TH and TTH at the point of injury, e.g., in pre-hospital settings, such as military far-forward operations, during transportation, in temporary and permanent medical facilities, and the like, early in the therapeutic window, e.g., less than about 30 minutes. The nasal cavity is well adapted to cooling the brain because its close proximity to the cavernous sinus and internal carotid artery and cerebrospinal fluid in the basal cistern which circulates through the brain. A tracheal intubated patient loses all cooling circulation through the nasal cavity which results in immediate warming of the brain. System 10 and method thereof reverses the warming effects of intubation and dramatically increases normal respiratory cooling effects by forcing a high volume of flow 16 of cooled air or breathable gas into the nasal cavity while automatically adjusting the cooling rate based on the temperature of the brain or a brain correlative site, e.g., using one or more temperature sensors 38, such as a tympanic temperature sensor, temporal artery sensor, or similar type sensor discussed above, to achieve rapid brain cooling and controlled hypothermia or normothermia.

The result is system 10 and the method thereof provides a less complex and less cumbersome system and method for cooling the brain discussed in the Background section above. System 10 and the method thereof provides a forced flow of cooled air or breathable gas that efficiently cools the brain to effectively provide TH and TTM to normothermic levels at the point of injury or prior to hospitalization and early in the therapeutic window, monitors the temperature of the brain and human subject, and adjusts temperature and flow rate of the flow of cooled air or breathable gas to reduce possible adverse side effects which may be associated with cooling the brain of a human subject.

Controller 32 shown in one or more of FIGS. 1 and 4 may be a processor, one or more processors, an application-specific integrated circuit (ASIC), firmware, hardware, and/or software (including firmware, resident software, microcode, and the like) or a combination of both hardware and software that may all generally be referred to herein as a "controller", which may be part of system 10 and method for cooling the brain of this invention. Computer program code for the programs for carrying out the instructions or operation of one or more embodiments of the system 10 and method and controller 32 may be written in any combination of one or more programming languages, including an object oriented programming language, e.g., C++, Smalltalk, Java, and the like, or conventional procedural programming languages, such as the "C" programming language or similar programming languages.

Figure 5:
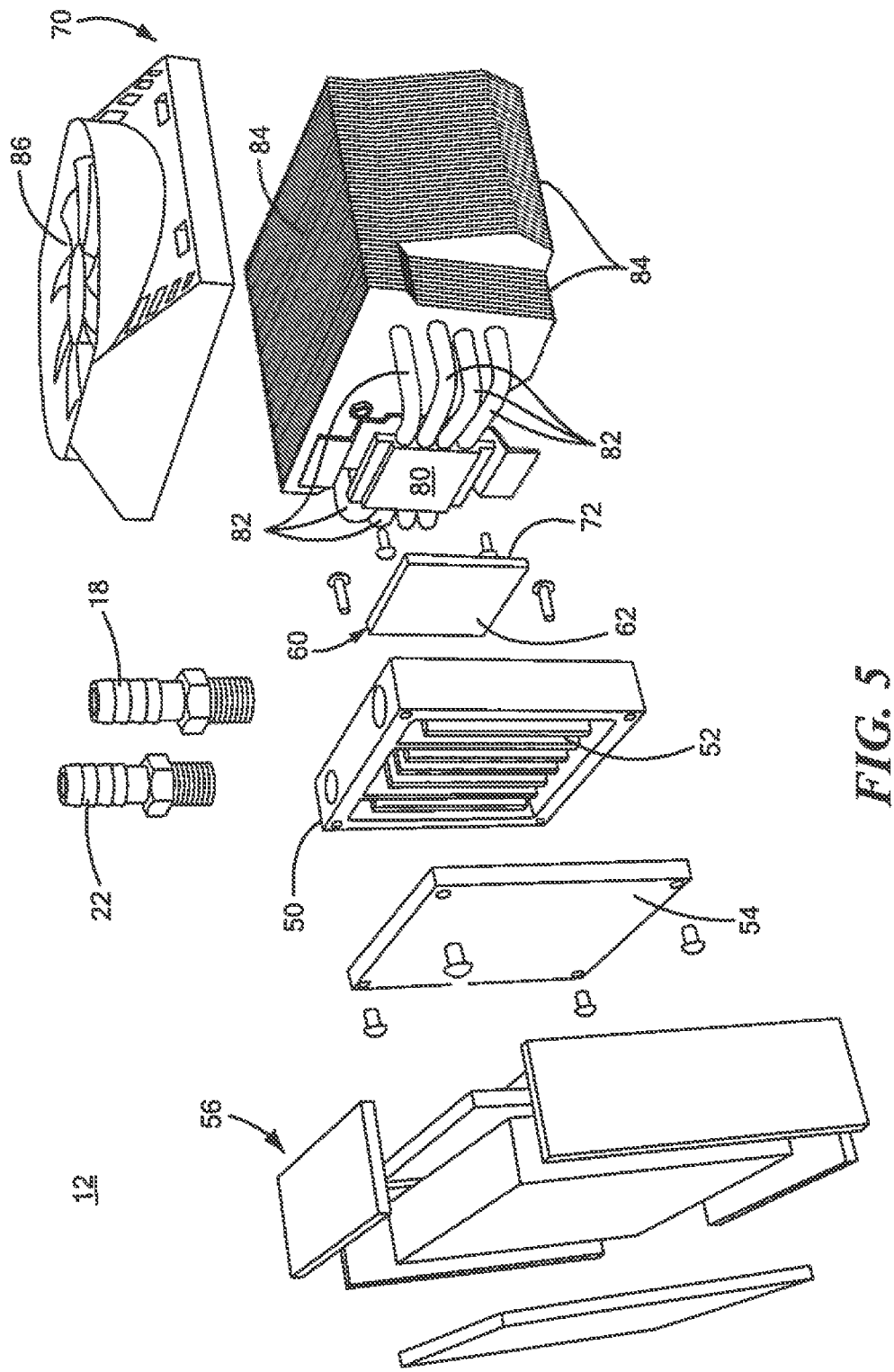
FIG. 5 is a three-dimensional view showing in further detail one example of a heat transfer subsystem and a heat exchange subsystem of the cooling subsystem shown in one or more of FIGS. 1-4.
Figure 6:
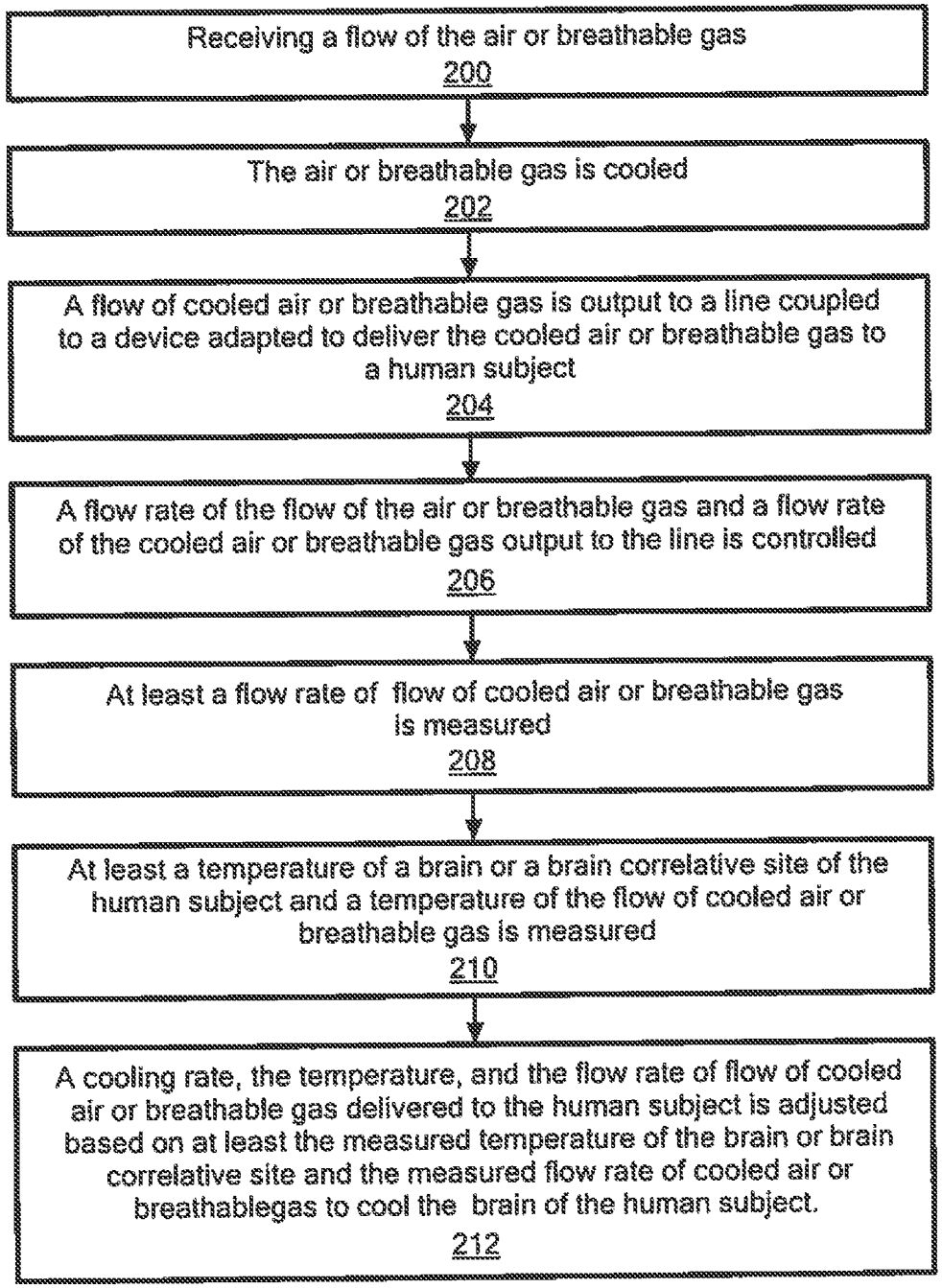
FIG. 6 is a block diagram showing one example of the primary steps of the method for cooling the brain of a human subject.

In one example, cooling subsystem 12, shown in one or more of FIGS. 1-4, preferably includes gas block 50, FIG. 5, coupled to input 18 and output 22, e.g., as shown in FIG. 3. Gas block 50, FIG. 5, preferably includes flow channels 52 which direct flow 14 of air or breathable gas 14, FIGS. 1 and 3, received at input 18, FIG. 3, through gas block 50, FIG. 5, where flow 14 of air or breathable gas 14 is cooled to create flow 16 of cooled air or breathable gas. Flow channels 52 direct flow 16 of cooled air or breathable gas to output 22, e.g., as shown in FIG. 3. Preferably, flow channels 52 are tight thermally conductive channels made of aluminum, copper, brass, steel, or similar type materials. Gas block 50 also includes cover 54. Cooling subsystem 12 may also include gas filter 56, FIGS. 3 and 5, which is preferably coupled to gas block 50.

In one design, cooling subsystem 12 also preferably includes heat transfer subsystem 60, FIGS. 3-5, configured to efficiently and effectively cool flow 14 of air or breathable gas, FIG. 3, to provide flow 16 of cooled air or breathable gas. In one design, heat transfer subsystem 60 is configured as thermoelectric cooler (TEC), FIG. 5, which is preferably based on the Peltier effect, to transfer heat from cold side 62 of TEC to flow 14 of air or breathable gas inside gas block 50 to effectively cool flow 14 of air or breathable gas to provide flow 16 of cooled air or breathable gas at outlet 22, e.g., as shown in FIGS. 1 and 3. Thus, the TEC of heat transfer system 60 preferably provides a temperature differential needed to effectively remove heat from flow 14 of air or breathable gas. In one example, the TEC of heat transfer subsystem 60 may be a commercially available TEC (available from TE Technology, Traverse City, Mich.) and is preferably rated to remove up to about 15 W of heat at 18 W of power or more. In other designs, heat transfer subsystem 60, FIG. 3, may utilize a refrigerant or heat transfer by radiation to transfer cold gas/liquid flow to cool flow 14 of air or breathable gas in gas block 50. The primary function heat transfer subsystem 60 is to remove heat from flow 14 of air or breathable gas received at input 18 and provide flow 16 of cooled air or breathable gas at outlet 22, as shown in FIGS. 1 and 3, which is delivered to human subject 28, e.g., by nasal cannula 26, FIG. 2, coupled to line 24 to effectively and efficiently cool the brain of human subject 28. The heat removed from flow 14 of air or breathable gas may be removed during flow or removed while in reserve mode.

Cooling subsystem 12 shown in one or more of FIGS. 1-4 also preferably includes heat exchanger subsystem 70, FIG. 5, coupled to heat transfer subsystem 60, e.g., a TEC. Heat exchanger subsystem 70 is preferably configured to remove heat from hot side 72 of the TEC and expel warm exhaust air or air or breathable gas 76, FIGS. 1 and 3, into the atmosphere as shown.

In another example, heat transfer subsystem 60, e.g., a TEC may be utilized as a heating subsystem to heat flow 14 of air or breathable gas and/or flow 16 of cooled air or breathable gas when the temperature thereof is too high. In one example, because the TEC of heat transfer subsystem 60 is a bipolar device, if the temperature of flow 14 of air or breathable gas, FIGS. 1 and 3, or flow 16 of cooled air or breathable gas is colder than desired, e.g., as set by controller 32, FIG. 4, and measured by one or more temperature sensors 38, the TEC of heat transfer subsystem 60 can be configured and controlled by controller 32 to control the current or the voltage applied to the TEC of heat transfer subsystem 60 such that cold side 62, FIG. 5, will become a hot side and heat flow 14 of air or breathable gas inside gas block 50 to increase the temperature of flow 16 of cooled air or breathable gas to provide the desired temperature of flow 16 of cooled air or breathable gas delivered via line 24, FIG. 2, to the device adapted to deliver flow 16 of cooled air or breathable gas to human subject 28, FIG. 2, e.g., a nasal cannular or similar type device.

In one design, heat exchanger subsystem 70, FIG. 5, preferably includes heat conductor block 80 coupled to hot side 72 of the TEC of heat transfer subsystem 60 and to conductive heat pipes 82 surrounded by conductive fins 84. Heat exchanger fan 86 is preferably coupled to conductive fins 84, e.g. as shown in FIG. 3. Heat conductor block 78 is preferably configured to efficiently remove heat from hot side 72 of the TEC of heat transfer subsystem 60. The heat from conductor block 80 is preferably transferred to conductive pipes 82 and cooled by conductive fins 84. Heat exchanger fan 86 removes the heat in conductive fins 84. In one design, heat conductor block 80, heat conductive pipes 82 and conductive fins 84 are made of a highly thermally conductive material, e.g., aluminum, copper, brass, steel, and the like. In another design, the warm air removed using the heat exchanger fan 86 or other flow over hot side 72 of the TEC of heat transfer subsystem 60 can be used to warm the human subject 28.

In one design, system 10 and the method thereof, shown in one or more of FIGS. 1-5, may include humidifier 96, FIG. 4, which preferably supplies moist air to line 24, FIG. 2, coupled to nasal cannula 26. In one design, a drip base system within line 24 may be utilized where intimate drops of liquid are provided into line 24 and swept with flow 16 of cooled air or breathable gas. In other examples, passing flow 16 of cooled air or breathable gas over a source of liquid may be utilized where flow 16 of cooled air or breathable gas is brought into contact with a liquid and not passed through it. In other examples, an in-line humidifier may be utilized.

In one design, user interface/display 34, FIGS. 1, 2 and 4 may provide a user interface for users of system 10 to provide input parameters to determine the various control options of system 10 and the method thereof discussed above. In one design, an LED or LCD screen may be utilized for a display that may be touch sensitive or use tactile visual and/or audio feedback buttons and preferably includes indicator light emitting devices or audible devices, such as buzzers or speakers.

One example of the method for cooling the brain of a human subject includes receiving a flow of the air or breathable gas, step 200, FIG. 1. The air or breathable gas is cooled, step 202. A flow of cooled air or breathable gas is output to a line coupled to a device adapted to deliver the cooled air or breathable gas to a human subject, step 204. A flow rate of the flow of the air or breathable gas and a flow rate of the cooled air or breathable gas output to the line is controlled, step 206. At least a flow rate of flow of cooled air or breathable gas is measured, step 208. At least a temperature of a brain or a brain correlative site of the human subject and a temperature of the flow of cooled air or breathable gas is measured, step 210. A cooling rate, the temperature, and the flow rate of flow of cooled air or breathable gas delivered to the human subject is adjusted based on at least the measured temperature of the brain or the brain correlative site and the measured flow rate of the flow of cooled air or breathable gas to cool the brain of the human subject, step 212.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A system for cooling the brain of a human subject, the system comprising:
   a cooling subsystem configured to input a flow of air or breathable gas, the cooling subsystem comprising a gas block including a surface in thermal communication with a thermal electric cooling (TEC) device and configured such that the flow of air or breathable gas contacts the gas block at a location in thermal communication with TEC to cool the air or breathable gas and output cooled air or breathable gas to a line coupled to a device adapted to deliver the cooled air or breathable gas to a human subject;
   a flow control device coupled to the cooling subsystem configured to control a flow rate of the flow of the air or breathable gas input to the cooling subsystem and a flow rate of the cooled air or breathable gas output to the line;

one or more flow rate sensors coupled to the cooling subsystem configured to measure at least a flow rate of flow of cooled air or breathable gas;

one or more temperature sensors configured to measure at least a temperature of a brain or a brain correlative site of the human subject and the temperature of the flow of cooled air or breathable gas; and a controller coupled to the cooling subsystem, the flow control device, the one or more flow rate sensors, and the one or more temperature sensors, the controller configured to adjust a cooling rate, the temperature, and the flow rate of flow of cooled air or breathable gas delivered to the human subject based on at least the measured temperature of the brain or the brain correlative site and the measured flow rate of the flow of cooled air or breathable gas to cool the brain of the human subject.

2. The system of claim 1 in which the controller is configured to adjust the temperature and the flow rate of the flow of cooled air or breathable gas to provide therapeutic hypothermic (TH) and/or target temperature management (TTM) to normothermic levels.

3. The system of claim 1 in which the controller is configured to control the flow control device to provide a flow rate of the cooled air or breathable gas at flow rate in the range of about 0 L/min to about 50 L/min.

4. The system of claim 1 in which the cooling subsystem cooling subsystem is configured to input the air or breathable gas having a temperature in the range of about −10° C. to about 10° C.

5. The system of claim 4 in which the controller is configured to control the cooling subsystem to cool the air or breathable gas and provide the flow of cooled air or breathable gas delivered to the human subject having a temperature in the range of about −14° C. to about 7° C.

6. The system of claim 1 in which the one or more temperature sensors includes a tympanic sensor or temporal artery sensor.

7. The system of claim 1 in which the device adapted to deliver the cooled air or breathable gas to a human subject includes a nasal cannula.

8. The system of claim 7 in which the one or more temperature sensors are adapted to be placed on an end of the nasal cannula.

9. The system of claim 1 in which the controller is configured to control the flow control device to adjust a pressure of the flow of cooled air or breathable gas.

10. The system of claim 1 in which the cooling subsystem includes a gas block comprised of a thermally conductive material, the gas block including an inlet configured to input the flow of air or breathable gas and an outlet configured to output the flow of cooled air or breathable gas.

11. The system of claim 10 in which the air block includes a plurality of flow channels comprised of the thermally conductive material configured to cool the flow of air or breathable gas and provide and direct the flow of cooled air or breathable gas to the outlet.

12. The system of claim 1 in which the cooling subsystem includes a heat transfer subsystem coupled to the gas block and configured as the thermal electric cooling (TEC) device.

13. The system of claim 12 in which the controller is configured to control a current or voltage applied to the TEC to provide a cooling temperature on a side of the TEC in contact with the gas block to cool the source of the flow of air or breathable gas and provide the flow of cooled air or breathable gas or to provide a heating temperature on a side of the TEC in contact with the gas block to heat the source of the flow of air or breathable gas to increase the temperature of the flow of cooled air or breathable gas.

14. The system of claim 13 further including a heat exchange transfer subsystem coupled to the heat transfer subsystem configured to remove heat from the heat transfer subsystem.

15. The system of claim 14 in which heat exchange transfer subsystem includes a conductor block coupled to a side of the TEC and conductive pipes coupled to conductive fins.

16. The system of claim 15 further including a fan coupled to the conductive fins.

17. A method for cooling the brain of a human subject, the method comprising:

receiving a flow of the air or breathable gas;

providing a cooling subsystem comprising a gas block including a surface in thermal communication with a thermal electric cooling (TEC) device and configured such that the flow of air or breathable gas contacts the gas block at a location in thermal communication with TEC to cool the air or breathable gas;

outputting a flow of cooled air or breathable gas to a line coupled to a device adapted to deliver the cooled air or breathable gas to a human subject;

controlling a flow rate of the flow of the air or breathable gas and a flow rate of the cooled air or breathable gas output to the line;

measuring at least a flow rate of flow of cooled air or breathable gas;

measuring at least a temperature of a brain or brain correlative site of the human subject and a temperature of the flow of cooled air or breathable gas; and adjusting a cooling rate, the temperature, and the flow rate of flow of cooled air or breathable gas delivered to the human subject based on at least the measured temperature of the brain or the brain correlative site and the measured flow rate of the flow of cooled air or breathable gas to cool the brain of the human subject.

18. The method of claim 17 further including adjusting the temperature and the flow rate of the flow of cooled air or breathable gas to provide therapeutic hypothermic (TH) and target temperature management (TTM) to normothermic levels.

19. The method of claim 17 further including providing a flow rate of cooled air or breathable gas at a flow rate in the range of about 0 to about 50 L/m.

20. The method of claim 17 further including receiving the flow of the air or breathable gas having a temperature in the range of about −10° C. to about 10° C.

21. The method of claim 20 further including cooling the flow of the air or breathable gas to a temperature in the range of about −14° C. to about 7° C.

22. The method of claim 17 in which the device adapted to deliver the flow of the air or breathable gas to the human subject includes a nasal cannula.

23. The method of claim 17 further including adjusting a pressure of the flow of cooled air or breathable gas.

24. The method of claim 17 further including providing a gas block comprised of a thermally conductive material, the gas block including an inlet to receive the flow of air or breathable gas and an outlet configured to output the flow of cooled air or breathable gas.

25. The method of claim 24 further including providing a heat transfer subsystem coupled to the gas block configured as the thermal electric cooling (TEC) device.

26. The method of claim 25 further including controlling a current or voltage applied to the TEC to provide a cooling temperature on a side of the TEC in contact with the gas block to cool the source of flow of air or breathable gas and provide a flow of cooled air or breathable gas or to provide a heating temperature on a side of the TEC in contact with the gas block to heat the source of flow of air or breathable gas to increase the temperature of the flow of cooled air or breathable gas.

27. The method of claim 26 further including providing a heat exchange transfer subsystem coupled to the heat transfer system configured to remove heat from the heat transfer subsystem.

\* \* \* \* \*